(12) United States Patent
Cheung et al.

(10) Patent No.: US 11,453,872 B2
(45) Date of Patent: Sep. 27, 2022

(54) DEVICE AND A METHOD FOR IMMOBILIZATION OF PROTEINS, ENZYMES OR CELLS

(71) Applicant: Bioright Worldwide Company Limited, Tortola (VG)

(72) Inventors: Chung Hong Cheung, Hong Kong (CN); Jun Wang, Hong Kong (CN); Junming Chen, Hong Kong (CN); Guilin Wang, Hong Kong (CN)

(73) Assignee: Bioright Worldwide Company Limited, Tortola (VG)

( * ) Notice: Subject to any disclaimer, the term of this patent is extended or adjusted under 35 U.S.C. 154(b) by 590 days.

(21) Appl. No.: 15/523,820

(22) PCT Filed: Oct. 28, 2015

(86) PCT No.: PCT/CN2015/093074
§ 371 (c)(1),
(2) Date: May 2, 2017

(87) PCT Pub. No.: WO2016/070738
PCT Pub. Date: May 12, 2016

(65) Prior Publication Data
US 2017/0321207 A1    Nov. 9, 2017

(30) Foreign Application Priority Data
Nov. 3, 2014    (CN) .......................... 201410608386.4

(51) Int. Cl.
C12M 1/40    (2006.01)
C12M 1/00    (2006.01)
C12N 11/06    (2006.01)
(Continued)

(52) U.S. Cl.
CPC ............... *C12N 11/06* (2013.01); *B01J 19/22* (2013.01); *C07K 1/042* (2013.01); *C07K 17/06* (2013.01);
(Continued)

(58) Field of Classification Search
CPC .......... C12N 11/06; C12N 11/02; B01J 19/22; C07K 1/042; C07K 17/06; C12M 21/18;
(Continued)

(56) References Cited

U.S. PATENT DOCUMENTS 4,016,811 A * 4/1977 Zavodny .................. B41N 7/04
101/148
4,893,999 A * 1/1990 Chmelir .................... B01J 19/22
264/212

(Continued)

FOREIGN PATENT DOCUMENTS

CH    665929 A  *  6/1988  ............. D06B 15/02
CN   1982445 A      6/2007
(Continued)

OTHER PUBLICATIONS

Smith et al., Optimize large methanol plants, 1984, Hydrocarbon Processing, 63(5), 95-100 (Year: 1984).*

*Primary Examiner* — Louise W Humphrey
*Assistant Examiner* — Anjali Ajit Hirani
(74) *Attorney, Agent, or Firm* — The Webb Law Firm

(57) ABSTRACT

Provided herein are a device and a method for preparation of immobilized proteins, enzymes or cells on a carrier to achieve the industrial batch production of the immobilized proteins, enzymes or cells.

24 Claims, 5 Drawing Sheets

(51) Int. Cl.
*C12N 11/02* (2006.01)
*B01J 19/22* (2006.01)
*C07K 1/04* (2006.01)
*C07K 17/06* (2006.01)
*C12M 1/12* (2006.01)
*C12M 1/26* (2006.01)

(52) U.S. Cl.
CPC ............ *C12M 21/14* (2013.01); *C12M 21/18* (2013.01); *C12M 25/00* (2013.01); *C12M 29/06* (2013.01); *C12M 33/00* (2013.01); *C12N 11/02* (2013.01)

(58) Field of Classification Search
CPC ...... C12M 25/00; C12M 29/06; C12M 33/00; C12M 21/14; B65H 49/24; B01F 7/00525; B21B 39/008
See application file for complete search history.

(56) References Cited

U.S. PATENT DOCUMENTS

| | | | | |
|---|---|---|---|---|
| 8,241,890 | B2* | 8/2012 | Stloukal | F26B 17/023 435/283.1 |
| 8,486,676 | B2 | 7/2013 | Jin et al. | |
| 2007/0087418 | A1* | 4/2007 | Mazeaud | C12N 11/14 435/117 |
| 2010/0028971 | A1* | 2/2010 | Jin | C12N 11/06 435/182 |
| 2014/0044790 | A1 | 2/2014 | Amoro et al. | |

FOREIGN PATENT DOCUMENTS

| | | | |
|---|---|---|---|
| CN | 202147994 U | * | 2/2012 |
| WO | 2011053959 A1 | | 5/2011 |

\* cited by examiner

DEVICE AND A METHOD FOR IMMOBILIZATION OF PROTEINS, ENZYMES OR CELLS

CROSS-REFERENCE TO RELATED APPLICATIONS

This application is the United States national phase of International Application No. PCT/CN2015/093074 filed Oct. 28, 2015, and claims priority to Chinese Patent Application No. 201410608386.4 filed Nov. 3, 2014, the disclosures of which are hereby incorporated in their entirety by reference.

BACKGROUND OF THE INVENTION

The present invention relates to the technical field of immobilization of proteins, enzymes or cells. Specifically, it relates to a device and a method for immobilization of proteins, enzymes or cells.

BACKGROUND ART

With the advance of biotechnology, proteins, enzymes or cells that contain enzymes are often used in an immobilized form in industry and other fields, as the immobilized form is easy to separate and recover from the products, allowed repeated usage and is more stable than the free enzyme. Many immobilization methods, such as physical adsorption, affinity linkage, covalent crosslinking, flocculation and encapsulation, are known to obtain the immobilized form of enzymes.

Specific activity (the activity of unit weight of an immobilized protein/enzyme/cell) is used to assess the efficiency of the immobilized protein/enzyme/cell. The specific activity is affected by both the immobilization method and specific surface area of the immobilized protein/enzyme/cell. Generally, larger specific surface area results in higher specific activity. For example, China patent publication CN1982445A discloses a carrier used for enzyme/cell immobilization and the immobilization method using the carrier. With using the porous organic foam material containing open pores as the carrier of immobilization of enzyme/cell, the specific surface area of immobilized enzyme/cell is increased in a large extent and hence increases the specific activity.

However, there is no report of device for preparation of the immobilized proteins/enzymes/cells in industrial batch production.

SUMMARY OF THE INVENTION

To overcome the shortcomings of the existing techniques, the invention provides a device and a method for preparation of immobilized proteins/enzymes/cells to immobilize proteins/enzymes/cells on the carrier to achieve the industrial batch production of the immobilized proteins, enzymes or cells.

A device for preparation of immobilized proteins, enzymes or cells, characterized in that the device comprises:
i) a conveyor belt that transports a carrier for immobilizing proteins, enzymes or cells;
ii) two or more spraying-kneading components that are arranged in sequence along a transport path of the conveyor belt; each of the spraying-kneading components includes the following components in sequence: (1) a spraying component that sprays a pre-prepared liquid for the immobilization of proteins, enzymes or cells on the surface of the carrier; (2) a kneading component that distributes the pre-prepared liquid evenly on the surface of the carrier;
iii) a squeezing component that removes the excess liquid remaining on the surface of the carrier after the carrier passes through the spraying-kneading components.

Preferably, the spraying component of each of the spraying-kneading components includes one or more sprayers that are provided above the conveyor belt, the one or more sprayers are arranged continuously and in sequence along the transport path of the conveyor belt, and the sprayers in the same spraying-kneading components spray the pre-prepared liquid of the same type.

Preferably, the sprayers include a sparger pipe, a spray nozzle or an overflow groove.

Preferably, the spray nozzle includes an atomizer nozzle or a flow nozzle.

Preferably, the sparger pipe includes holes for spraying the pre-prepared liquid and a wire gauze is covered on the holes.

Preferably, the spraying component includes one or more first height adjustment mechanism sets that adjust the heights of the sprayers above the conveyor belt, and each of the first height adjustment mechanism sets includes two first height adjustment mechanisms that are provided on both ends of the sprayer that corresponds to the first height adjustment mechanism set.

Preferably, the kneading component of each of the spraying-kneading components includes one or more kneading rolls that are provided above the conveyor belt, the one or more kneading rolls are arranged along the transport path of the conveyor belt continuously and in sequence, and each of the kneading rolls rolls over the surface of the carrier when the carrier passes through a gap between the kneading roll and the conveyor belt.

Preferably, the number of the kneading rolls is one; the kneading roll is smooth on its surface or possesses uniformly distributed grooves.

Preferably, the number of the kneading rolls is more than one, some of the kneading rolls are smooth on their surfaces and the others of the kneading rolls possess uniformly distributed grooves; or all of the kneading rolls are smooth on their surfaces; or all of the kneading rolls possess uniformly distributed grooves.

Preferably, the grooves are strip-shaped, a lengthwise direction of grooves is parallel to an axial direction of the kneading roll, and the grooves are distributed evenly in a circumferential direction of the kneading rolls; or the grooves are ring-shaped, a circumferential direction of the grooves is perpendicular to the axial direction of the kneading rolls and the grooves are distributed evenly in the axial direction of the kneading rolls.

Preferably, for two adjacent kneading rolls that have the ring-shaped grooves, the ring-shaped grooves of one of the adjacent kneading rolls are offset by a width of one groove with respect to the ring-shaped grooves of the other kneading roll respectively.

Preferably, the shape of the grooves is trapezoidal, rectangular or tapered.

Preferably, the kneading component includes one or more second height adjustment mechanism sets that adjust heights of the kneading rolls above the conveyor belt; each of the second height adjustment mechanism sets includes two second height adjustment mechanisms that are provided on both ends of the kneading roll that corresponds to the second height adjustment mechanism set.

Preferably, the squeezing component includes one or more squeezing rolls that are provided above the conveyor belt, the one or more squeezing rolls are arranged along the transport path of the conveyor belt continuously and in sequence, and each of the squeezing rolls over the surface of the carrier to remove the excess liquid when the carrier passes through a gap between the squeezing roll and the conveyor belt.

Preferably, the squeezing component includes one or more squeezing roll sets that are provided continuously and in sequence at a terminal end of the conveyor belt, the one or more squeezing roll sets are arranged along the transport path of the conveyor belt; each of the squeezing roll sets includes an upper squeezing roll and a lower squeezing roll, wherein the carrier that reaches the terminal end of the conveyor belt, passes through a gap between the upper squeezing roll and the lower squeezing roll by the rotation of the lower squeezing roll, a linear velocity of the lower squeezing roll is equal to that of the conveyor belt, and the upper squeezing roll rolls over the carrier to remove the excess liquid when the carrier passes therefrom.

Preferably, the squeezing component includes one or more third height adjustment mechanism sets that adjust heights of the squeezing rolls above the conveyor belt, and each of the third height adjustment mechanism sets includes two third height adjustment mechanisms that are provided on both ends of the squeezing roll that corresponds to the third height adjustment mechanism set.

Preferably, the squeezing component includes one or more third height adjustment mechanism sets that adjust the heights of the upper squeezing rolls above the lower squeezing rolls, and each of the third height adjustment mechanism sets includes two third height adjustment mechanisms that are provided on both ends of the squeezing roll that corresponds to the third height adjustment mechanism set.

Preferably, the device further comprises a motor that provides power; and a transmission mechanism that delivers the power from the motor to the lower squeezing roll and the conveyor belt.

Preferably, the device further comprises a motor that provides power; and a transmission mechanism that delivers the power from the motor to the conveyor belt.

Preferably, the device further comprises a recovery support plate that supports the carrier after the carrier passes through the squeezing component.

Preferably, the carrier is made of a porous organic foam material containing open pores.

Preferably, the carrier is made of melamine.

Preferably, the carrier is sheet-shaped with a thickness of 0.1-2 cm.

As another technical aspect, the invention also discloses a method for preparation of immobilized proteins, enzymes or cells using the device provided in the invention to prepare immobilized proteins, enzymes or cells.

Preferably, the method comprises the following steps:
S1. to prepare a liquid mixture of proteins, enzymes or cells and a crosslinker by crosslinking the proteins, enzymes or cells using the crosslinker;
S2. to spray the liquid mixture on the surface of the carrier and distribute the liquid mixture evenly on the surface of the carrier;
S3. to spray a flocculant on the surface of the carrier and distribute the flocculant evenly on the surface of the carrier;
S4. to remove the excess liquid remaining on the surface of the carrier.

Preferably, the concentration of the proteins or the enzymes is 0.3%-30%.

Preferably, the concentration of the cells is 0.5%-50%.

Preferably, the crosslinker is a polyaldehyde compound.

Preferably, the polyaldehyde compound is glutaraldehyde or dialdehyde starch.

Preferably, the flocculant is polyethyleneimine (PEI) or chitosan.

The invention has following advantages:

The invention provides a device for preparation of immobilized proteins, enzymes or cells. The device uses the conveyor belt to transport the carrier for immobilization. During transportation, two or more spraying-kneading components that are arranged in sequence along the transport path of the conveyor belt perform two or more cycles of loading and kneading. i.e. firstly, the spraying component sprays a pre-prepared liquid for immobilization on the surface of the carrier; secondly, the kneading component distributes the pre-prepared liquid evenly on the surface of the carrier to immobilize the proteins, enzymes or cells on the carrier. Using the device provided in the invention, the industrial batch production of the immobilized proteins, enzymes or cells are achieved.

The invention provides a device for preparation of immobilized of proteins, enzymes or cells to immobilize proteins, enzymes or cells on the carrier to achieve the industrial batch production of the immobilized proteins, enzymes or cells.

DETAILED DESCRIPTION OF THE INVENTION

Figure 1:
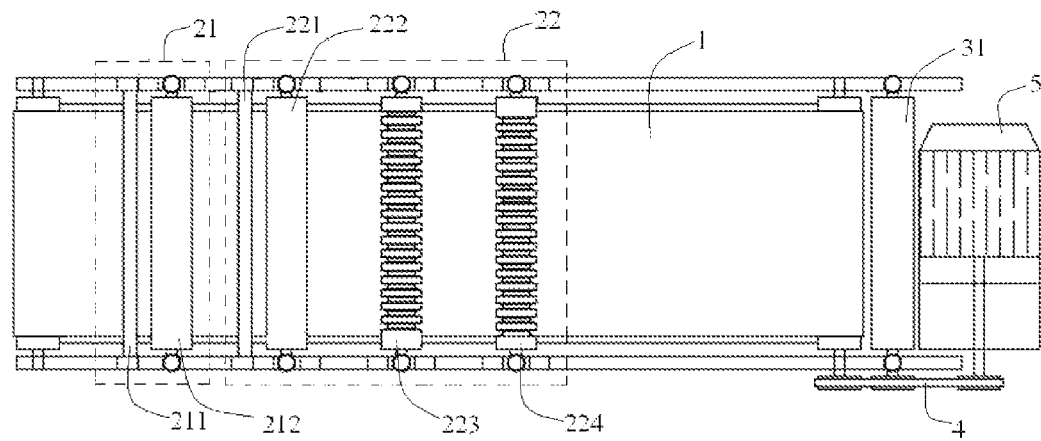
FIG. 1 is a vertical view of a device for preparation of immobilized proteins, enzymes or cells provided in the invention.

In order that a person skilled in the art understands the technical solution of the invention, a detail description combined with the drawings is provided to illustrate the device and the method for preparation of immobilized proteins, enzymes or cells.

The invention provides a device for preparation of immobilized proteins, enzymes or cells; the device comprises a conveyor belt, two or more spraying-kneading components and a squeezing component. The conveyor belt transports a carrier for immobilizing proteins, enzymes or cells; two or more spraying-kneading components that are arranged in sequence along a transport path of the conveyor belt perform two or more cycles of loading and kneading when the carrier passes through the spraying-kneading components one by one during transportation from one end of the conveyor belt to the other end of the conveyor belt. Each of the spraying-kneading components includes a spraying component and a kneading component in sequence. When the carrier passes through the spraying component and the kneading component in this order, at first, the spraying component sprays the pre-prepared liquid for immobilization on the surface of the carrier, and then the kneading component distributes the pre-prepared liquid evenly on the surface of the carrier. The squeezing component removes the excess liquid remaining on the carrier after the carrier passes through the spraying-kneading components. The above steps are repeated until an appropriate amount of proteins, enzymes or cells is immobilized on the carrier.

It should be noted that for the immobilization of proteins, enzymes or cells, it is often required to load two or more types of liquids on the carrier in sequence. After the first type of liquid is loaded on the carrier, one or more times of kneading is performed before the next type of the liquid is loaded, to ensure the first type of liquid is evenly distributed on the surface of carrier. In addition, in the same spraying-kneading component, liquid of the same type may be sprayed one time or sprayed continuously two or more times by the spraying component, followed by the continuous kneading of one or more times by the kneading component; or liquid of the same type can be sprayed on the carrier two or more times discontinuously, that is, the kneading is performed continuously one or more times by the kneading component within an interval between two times of spraying. In summary, the number of the spraying-kneading components is decided by the number of the types of liquid to be loaded; and the number of times and the order of the spraying and the kneading performed by each spraying-kneading component are set and combined according to requirement of the actual situation. Thus, using the device provided in the invention, the industrial batch production of the immobilized proteins, enzymes or cells are achieved.

The detail description of the device for preparation of immobilized proteins, enzymes or cells is given below with the aid of FIGS. 1 to 6B.

Figure 2:
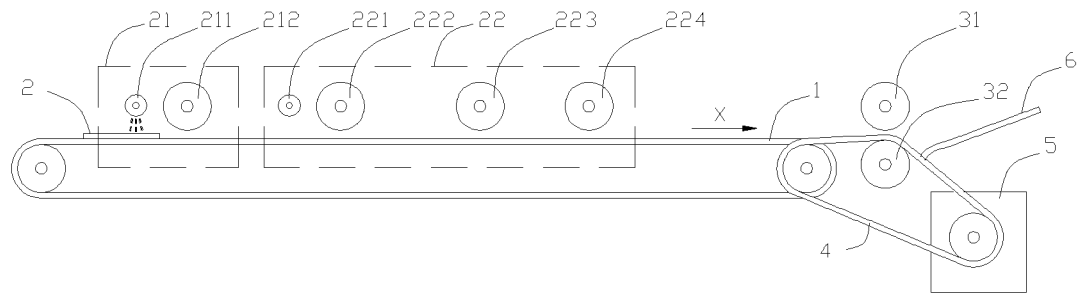
FIG. 2 is a front view of the device for preparation of immobilized proteins, enzymes or cells provided in the invention.

The device for preparation of immobilized proteins, enzymes or cells provided in the embodiment comprises a conveyor belt 1, two spraying-kneading components 21, 22 and a squeezing component. The conveyor belt 1 transports a carrier 2 for immobilizing proteins, enzymes or cells from a left end thereof to a right end thereof along a direction X as shown in FIG. 2. During transportation, the carrier 2 passes through the two spraying-kneading components 21, 22 that are arranged in sequence along a transport path of the conveyor belt 1 to perform loading and kneading of two pre-prepared liquids. For example, the first spraying-kneading component 21 performs spraying and kneading of a liquid mixture of proteins, enzymes or cells and a crosslinker; the second spraying-kneading component 22 performs spraying and kneading of a flocculant that precipitates the crosslinked proteins, enzymes or cells on the carrier to complete the immobilization reaction.

As indicated in FIGS. 1 and 2, the spraying component of the first spraying-kneading component 21 comprises a sprayer 211 and a kneading roll 212 that are provided in sequence above the conveyor belt 1; the spraying component of the second spraying-kneading component 22 comprises a sprayer 221 and three kneading rolls 222, 223, 224. The sprayer 211 sprays the liquid mixture of the proteins, enzymes or cells and the crosslinker toward the surface of the carrier 2 that passes therefrom; the kneading roll 212 rolls over the surface of the carrier 2 to distribute the liquid mixture evenly on the surface of the carrier 2 when the carrier 2 passes through a gap between the kneading roll 212 and the conveyor belt 1 to complete spraying and kneading of the liquid mixture. The sprayer 221 sprays the flocculant on the surface of the carrier 2 that passes therefrom; the three kneading rolls 222, 223, 224 roll over the surface of the carrier 2 in sequence to distribute the flocculant evenly on the surface of the carrier 2 to complete the immobilization reaction.

Figure 3:
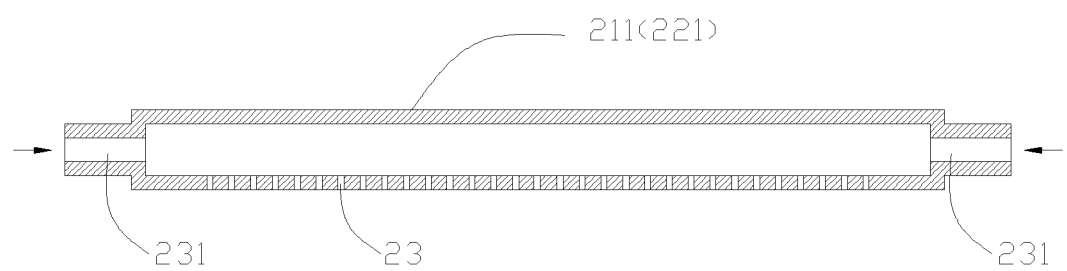
FIG. 3 is a section view of a sparger pipe of the device for preparation of immobilized proteins, enzymes or cells provided in the invention.

In the embodiment, each of the two sprayers 211, 221 is a sparger pipe. A section view of the sparger pipe used in the embodiment is shown in FIG. 3. The sparger pipe is hollow-structured and has two entrances 231 located on its both ends for the liquid mixture or the flocculant to enter. A row of holes 23 that are arranged along an axial direction of the sparger pipe are provided on a pipe wall of the sparger pipe. The row of holes 23 faces to the conveyor belt 1 to spray the liquid mixture or the flocculant on the surface of the carrier 2 when the carrier 2 passes therefrom. The structure of the holes 23 in the embodiment is just exemplary; in practical application, the shape and the diameter of each hole and the distance between the holes are decided in consideration of the desired speed, angle and amount of the spraying.

It should be noted that in practical application, the sprayer can use a spray nozzle structure such as an atomizer nozzle or a flow nozzle or use another spraying structure such as an overflow groove. Preferably, a wire gauze is covered on the holes of the sparger pipe, the spray nozzle or the notch of the overflow groove for even spraying.

Figure 6A:
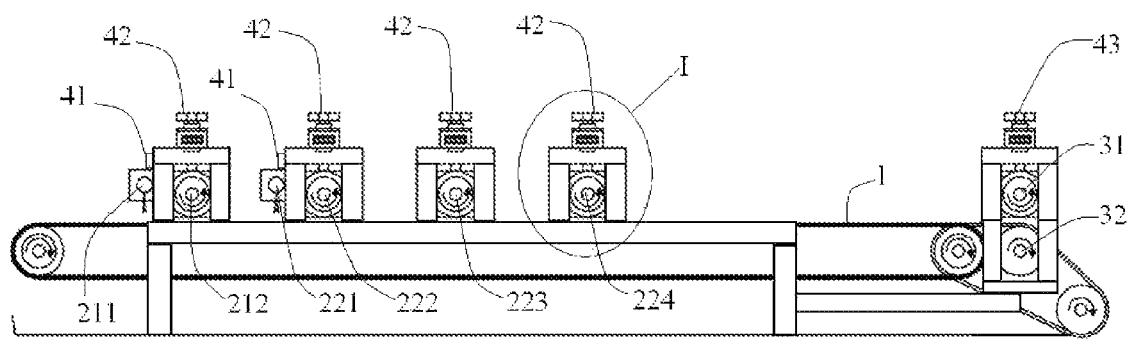
FIG. 6A is a schematic diagram showing that the device for preparation of immobilized proteins, enzymes or cells provided in the invention is installed with height adjustment mechanisms.
Figure 6B:
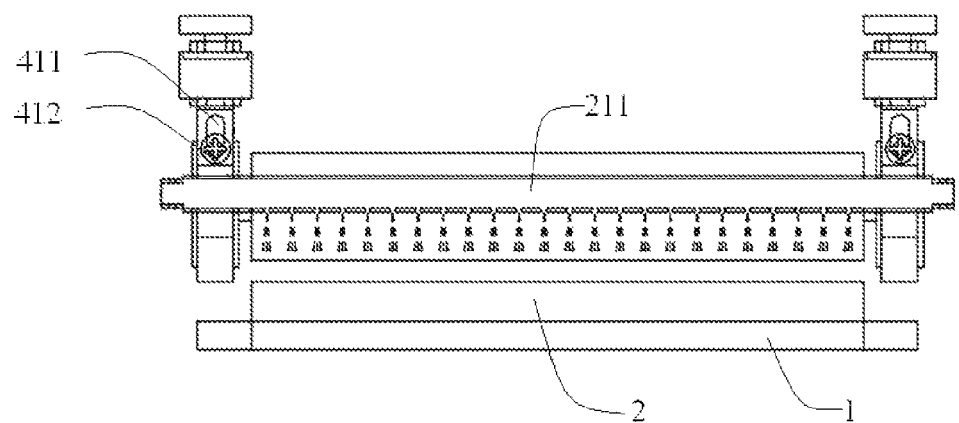
FIG. 6B is a schematic diagram of a first height adjustment mechanism in FIG. 6A.

Preferably, referring to FIGS. 6A and 6B, the spraying component further includes first height adjustment mechanism sets, the number of the first height adjustment mechanism sets corresponds to the number of the sprayers, and the first height adjustment mechanism sets adjust heights of the sprayers above the conveyor belt 1. In the embodiment, two first height adjustment mechanism sets adjust the heights of the two sprayers 211, 221 above the conveyor belt 1 respectively. The ideal height of each sprayer above the conveyor belt 1 is adjusted according to the thickness of the carrier 2 to improve the flexibility of the device. Each of the first height adjustment mechanism sets includes two first height adjustment mechanisms 41 that are provided on both ends of the sprayer 211. As shown in FIG. 6B, each of the first height adjustment mechanisms 41 is specifically configured to include a slide rail 411 and a locking bolt 412. The slide rail 411 is provided to a stand located on both sides of the conveyor belt 1; a slider that can slide up and down relative to the conveyor belt 1 along slide rail 411 encases the sprayer 211; the locking bolt 412 fixes the position of the sprayer 211 when the sprayer 211 reaches an appropriate height.

It should be noted that the structure of the first height adjustment mechanism set for the sprayer 211 is similar to the structure of the first height adjustment mechanism set for the sprayer 221. The structure of the first height adjustment mechanisms 41 is not limited to the structure described in the embodiment. In practical application, the first height adjustment mechanism is not restricted particularly as long as it can adjust the heights of the sprayers above the conveyor belt.

Figure 4:
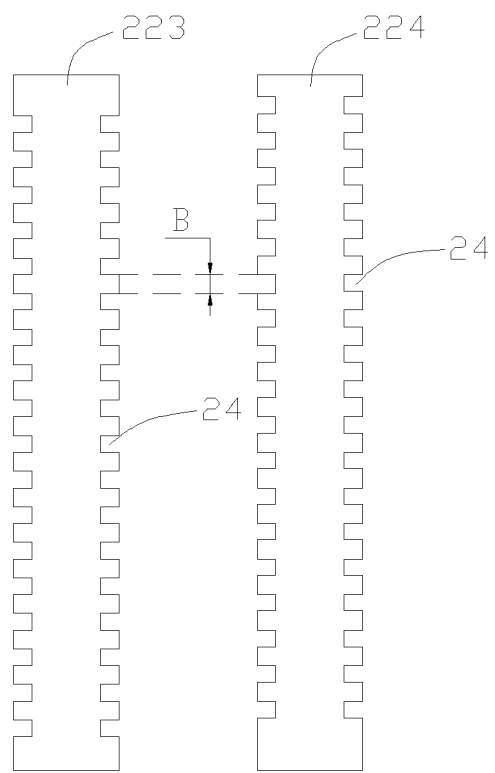
FIG. 4 is a schematic diagram of two kneading rolls of the device for preparation of immobilized proteins, enzymes or cells provided in the invention.

A detail description of the structure of the kneading roll is given below. As shown in FIG. 1, the kneading component of the first spraying-kneading component 21 includes one kneading roll 212 that are smooth on its surface; the kneading component of the second spraying-kneading component 22 includes three kneading rolls 222, 223, 224. The kneading roll 222 is smooth on its surface and the other two kneading rolls 223, 224 have a plurality of grooves 24 distributed evenly on their surfaces. As shown in FIG. 4, the grooves 24 are ring-shaped, a circumferential direction of the grooves is perpendicular to an axial direction of the kneading roll(s), and the grooves are distributed evenly in the axial direction of the kneading roll(s). The shape of the grooves 24 can be trapezoidal, rectangular or tapered. Preferably, for the two adjacent kneading rolls 223, 224, the ring-shaped grooves 24 of the kneading roll 223 are offset by a width B of one groove with respect to the ring-shaped grooves 24 of the kneading roll 224 respectively. It allows the two kneading rolls 223, 224 to roll over different parts on the surface of the carrier 2, instead of rolling over the same part of the carrier, thus to get even kneading.

In practical application, the number of the kneading rolls in each kneading component is determined according to the actual demand. It may be selected so that some of the kneading rolls are smooth on their surfaces and others of the kneading rolls have the grooves distributed evenly on their surfaces; or all of the kneading rolls are smooth on their surfaces; or all of the kneading rolls have uniformly distributed grooves on their surfaces.

Figure 5A:
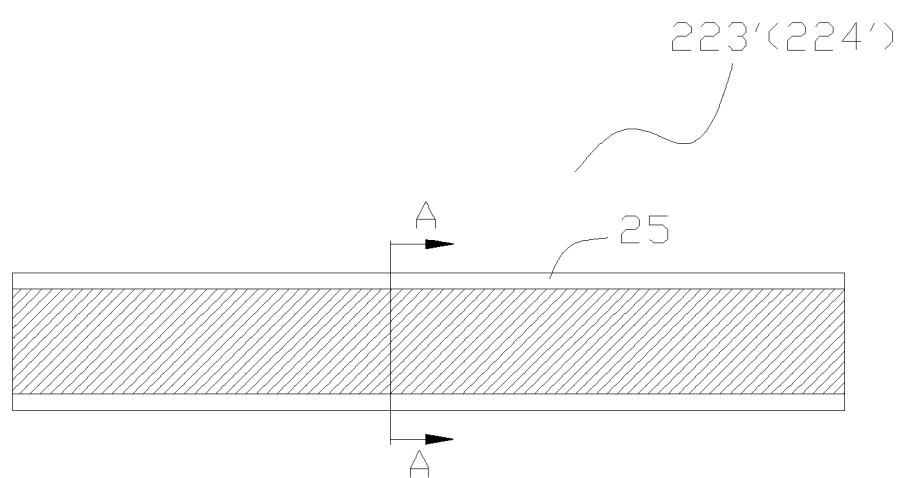
FIG. 5A is a front view of a kneading roll of another type.
Figure 5B:
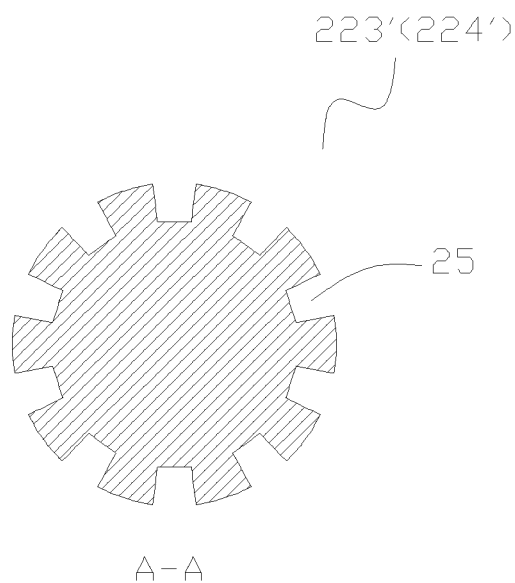
FIG. 5B is a section view taken along a line A-A in FIG. 5A.

In the embodiment, the grooves are ring-shaped, the circumferential direction of the grooves is perpendicular to the axial direction of the kneading rolls and the grooves are distributed evenly in the axial direction of the kneading rolls. However, it should be noted that the invention is not limited to this. In the practical application, the grooves of the kneading rolls can be made as shown in FIGS. 5A and 5B. The surface of the kneading roll 223' or 224' contains a plurality of grooves 25. The grooves 25 are strip-shaped, a lengthwise direction of the grooves is parallel to an axial direction of the kneading roll 223' or 224', and the grooves are distributed evenly in a circumferential direction of the kneading roll 223' or 224'. A groove of another type in any form can be chosen according to the actual demand.

Figure 6C:
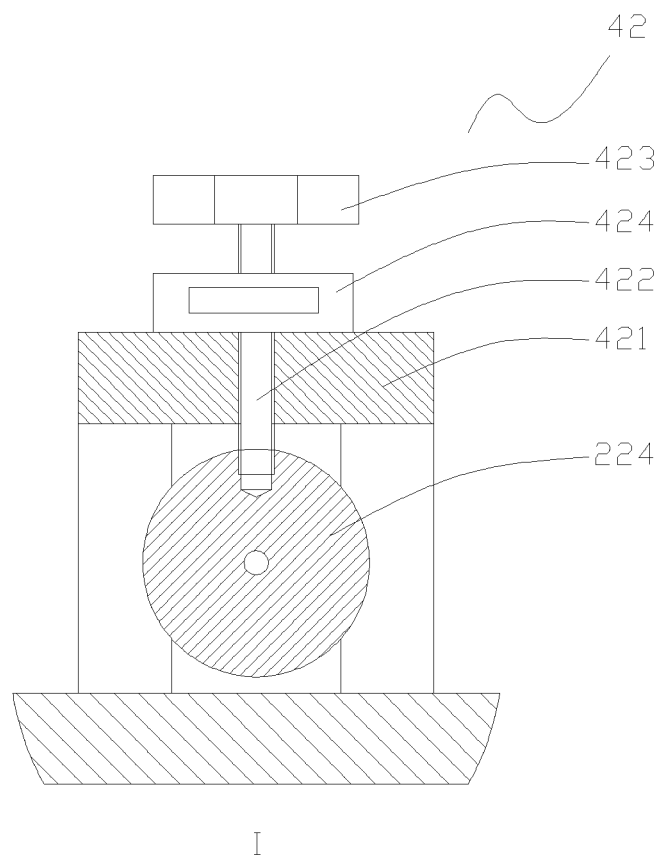
FIG. 6C is a section view of a second or third height adjustment mechanism in FIG. 6A.

Preferably, referring to FIGS. 6A and 6C, the kneading component further includes one or more second height adjustment mechanism sets, the number of the second height adjustment mechanism sets corresponds to the number of the kneading rolls, and the second height adjustment mechanism sets adjust heights of the kneading rolls above the conveyor belt 1. In the embodiment, four second height adjustment mechanism sets adjust the heights of the four kneading rolls 212, 222, 223, 224 above the conveyor belt 1. The ideal height of each kneading roll above the conveyor belt 1 is adjusted according to the thickness of the carrier 2 to improve the flexibility of the device. Each of the second height adjustment mechanism sets includes two second height adjustment mechanisms 42 that are provided on both ends of the kneading roll. As shown in FIG. 6C, each of the second height adjustment mechanism 42 is specifically configured to include a stud 422, a handwheel 423 and a height adjustment indicator 424. A screw-threaded hole 421 is provided in the stand located on the both sides of the conveyor belt 1, and the stud 422 mates with the screw-threaded hole 421 and is in threaded connection with installing members (not shown in the figure) for the kneading roll 224; by rotating the handwheel 423 that is fixed on the top of the stud 422 clockwise or anti-clockwise, the stud 422 drives the kneading roll 224 to move up and down relative to the conveyor belt 1. The structure of the other kneading rolls can be the same as that of the kneading roll 224. The ideal height of each kneading roll above the conveyor belt 1 is adjusted by the second height adjustment mechanisms 42 according to the thickness of the carrier 2 to improve the flexibility of the device. The height adjustment indicator 424 indicates the heights of the kneading rolls to make sure the heights of kneading rolls are adjusted accurately.

It should be noted that the structure of the second height adjustment mechanism 42 is not limited to the structure described in the embodiment. In practical application, the second height adjustment mechanism is not restricted particularly as long as it can adjust the heights of the kneading rolls above the conveyor belt.

The squeezing component removes the excess liquid remaining on the carrier after the carrier passes through the spraying-kneading components. In the embodiment, referring to FIGS. 1 and 2, the squeezing component includes one squeezing roll set that is provided at the terminal end (right end) of the conveyor belt 1. The squeezing roll set includes an upper squeezing roll 31 and a lower squeezing roll 32. The carrier 2 that reaches the terminal end of the conveyor belt 1 passes through a gap between the upper squeezing roll 31 and the lower squeezing roll 32 by the rotation of the lower squeezing roll 32. A linear velocity of the lower squeezing roll 32 is equal to that of the conveyor belt 1; the upper squeezing roll 31 rolls over the surface of the carrier 2 to remove the excess liquid when the carrier 2 passes therefrom. The gap between the upper squeezing roll 31 and the lower squeezing roll 32 is level with the surface of the conveyor belt 1 to allow the carrier 2 to be aligned with and enter the gap between the upper squeezing roll 31 and the lower squeezing roll 32 accurately when the carrier 2 is transported to the terminal end of the conveyor belt 1. The lower squeezing roll 32 is a drive wheel and the upper squeezing roll 31 is a driven wheel. That is, the lower squeezing roll 32 functions to transport the carrier similarly to the conveyor belt 1. The upper squeezing roll 31 rolls to rub against the surface of the carrier 2 when the carrier passes therefrom, and the excess liquid remaining on the surface of the carrier is removed.

Preferably, the conveyor belt 1 and the lower squeezing roll 32 is driven synchronously by a motor 5 and a transmission mechanism 4 to ensure their linear velocities are equal to one another. Specifically, the motor 5 provides power; the transmission mechanism 4 delivers the power from the motor 5 to the conveyor belt 1 and the lower squeezing roll 32 simultaneously. In the embodiment, the transmission mechanism 4 is a belt drive including a synchronous belt and a drive wheel. Under the driving of the motor 5, the drive wheel delivers the power to the conveyor belt 1 and the lower squeezing roll 32 with the synchronous belt to allow them to rotate at the same speed. In practical application, the transmission mechanism 4 can be a drive of another type, for example a wheel drive, a chain drive, etc, as long as the conveyor belt 1 and the lower squeezing roll 32 rotate at the same speed.

It should be noted that the number of the squeezing roll set is not limited to one as in the embodiment. In practical application, more than one squeezing roll sets that are arranged in sequence in the transport direction of the conveyor belt to squeeze the carrier multiple times is allowed.

Preferably, as shown in FIG. 6A, the squeezing component includes one or more third height adjustment mechanism sets, the number of the third height adjustment mechanism sets corresponds to the number of the squeezing rolls to adjust heights of the upper squeezing rolls above the lower squeezing rolls. Each of the third height adjustment mechanism sets includes two third height adjustment mechanisms 43 that are provided on both ends of the upper squeezing roll. The structure of the third height adjustment mechanisms 43 is similar to the structure of the second height adjustment mechanisms 42 that adjusts the heights of the kneading rolls and is not described repeatedly.

Figure 7:
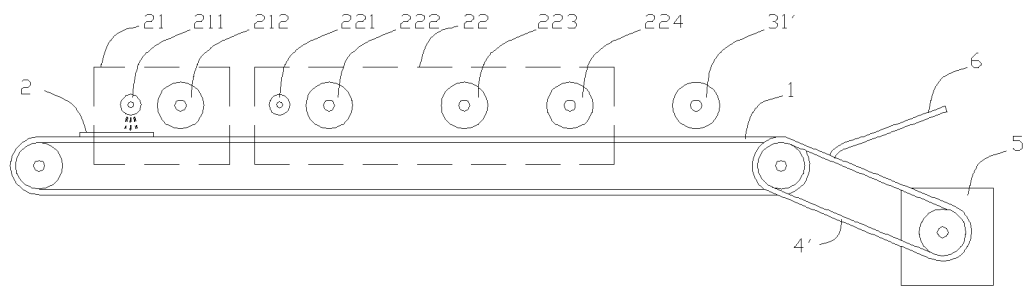
FIG. 7 is a schematic diagram of a squeezing component of another type of the device provided in the invention.

As a modified embodiment of the squeezing component in the embodiment, FIG. 7 shows a schematic diagram of a squeezing component of another type. Referring to FIG. 7, the squeezing component includes one squeezing roll 31' that is provided above the conveyor belt 1, and the squeezing roll 31' rolls over the surface of the carrier 2 to remove the excess liquid when the carrier 2 passes through a gap between the squeezing roll 31' and the conveyor belt 1. Compared with the previous embodiment, the modified embodiment cancels the lower squeezing roll and only uses the upper squeezing roll that is provided above the conveyor belt 1 and downstream the spraying-kneading components. The excess liquid on the surface of the carrier 2 can also be removed by simply providing power to transport rolls of the conveyor belt 1 so that a device that is simple and compact in structure and stable in transportation is obtained. For example, a structure of a transmission mechanism 4' is shown in FIG. 7, the transmission mechanism 4' provides power from the motor 5 to the conveyor belt 1.

In practical application, it is possible that squeezing rolls 31' with the number of two, three, four or more that are arranged continuously and in sequence in the transport direction of the conveyor belt 1 squeeze the carrier 2 two or more times. For the squeezing component in the modified embodiment, the third height adjustment mechanism sets adjust the heights of the squeezing rolls 31' above the conveyor belt 1.

In addition, in the embodiment, a recovery support plate 6 is installed at the terminal end of the conveyor belt 1 to receive the carrier 2 after the carrier passes through the squeezing component. Preferably, the surface for supporting the carrier 2 of the recovery support plate 6 can be inclined upwardly toward the surface of the conveyor belt 1 to prevent the carrier 2 that moves onto the recovery support plate 6 from falling off. After the carrier 2 is taken out of the recovery support plate 6, the carrier 2 is sent back to an initial end of the conveyor belt 1 to repeat the above immobilization procedure until an appropriate amount of proteins, enzymes or cells is immobilized on the carrier 2. In practical application, the surface for supporting the carrier 2 of the recovery support plate 6 can be horizontal.

In the embodiment, the carrier 2 is made of a porous organic foam material containing open pores such as melamine. Preferably, the carrier 2 is sheet-shaped with a thickness of 0.1-2 cm. Using the porous organic foam material containing open pores increases the specific surface area of the immobilized proteins, enzymes or cells largely, and hence increases the specific activity of immobilized proteins, enzymes or cells remarkably. The porous organic foam material is an inert material that is less prone to break and inexpensive and hence the production cost is reduced. In practical application, the carrier can be made to have various shapes and sizes without changing the specific surface area to be adapted to the device for preparation of immobilized proteins, enzymes or cells provided in the invention for achieving the industrial batch production of the immobilized proteins, enzymes or cells.

It should be noted that the number of the spraying-kneading components is not limited to two. In reality, the number of the spraying-kneading components is determined according to different immobilization methods. In practical application, the number of the spraying-kneading components can be three or more depending on different immobilization methods. Moreover, the types of the pre-prepared liquids of each spraying-kneading component and the sequence of the spraying of the pre-prepared liquids can be varied for different immobilization methods.

As another technical solution, the invention provides a method for preparation of immobilized proteins, enzymes or cells using the device to prepare immobilized proteins, enzymes or cells provided in this invention to achieve the industrial batch production of the immobilized proteins, enzymes or cells.

Figure 8:
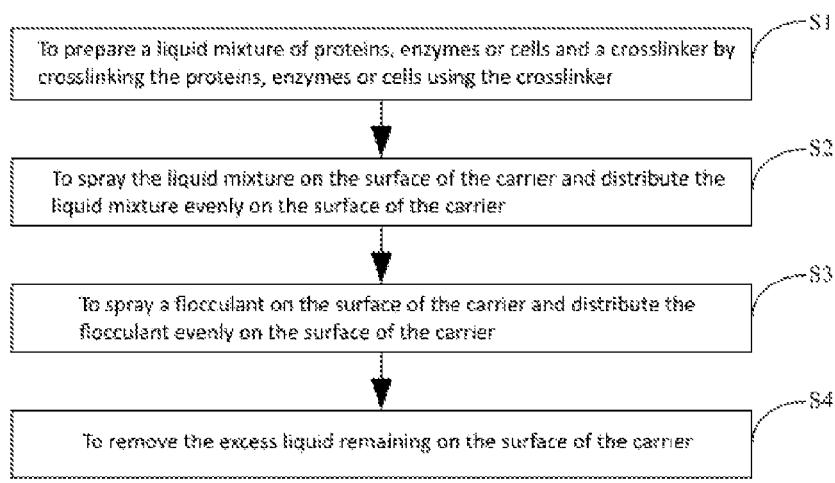
FIG. 8 is a flow chart of an immobilization method provided in the invention.

Preferably, FIG. 8 shows a flow chat of the immobilization method used in the embodiment. Referring the FIG. 8, for the device for preparation of immobilized proteins, enzymes or cells provided in the invention, the immobilization method comprises the following steps:

S1. to prepare a liquid mixture of proteins, enzymes or cells and a crosslinker by crosslinking the proteins, enzymes or cells using the crosslinker;

S2. to spray the liquid mixture on the surface of the carrier and distribute the liquid mixture evenly on the surface of the carrier;

S3. to spray a flocculant on the surface of the carrier and distribute the flocculant evenly on the surface of the carrier;

S4. to remove the excess liquid remaining on the surface of the carrier.

Preferably, in the above immobilization method, the concentration of the proteins or the enzymes is 0.3%-30%; the concentration of the cells is 0.5%-50%; for example, the crosslinker is a polyaldehyde compound that is preferably glutaraldehyde or dialdehyde starch; the flocculant is polyethyleneimine (PEI) or chitosan.

Two examples for further illustration of the immobilization method in the invention are presented in detail below.

Example 1

Immobilization of *E. coli* Cells Containing Expressed Glucose Isomerase

Twenty five g of *E. coli* cells containing expressed glucose isomerase (Refers to China patent publication CN1982445A for details) was resuspended in 175 ml of deionized water. Twenty ml of 1% (v/v) glutaraldehyde solution was added into the deionized water after resuspension of *E. coli* cells; and the liquid mixture was stirred for 10 minutes. The device that has two spraying-kneading components described above was used to prepare the immobilized cells. The procedure included the following steps:

The liquid mixture of the cells and glutaraldehyde was sprayed by the spraying component of the first spraying-kneading component at a flow rate of 60 ml/min; 0.25% (w/v) PEI solution was sprayed by the spraying component of the second spraying-kneading component at a flow rate of 30 ml/min; a transport speed of conveyor belt was set to 80 cm/min. The carrier was made of 1 g of melamine foam with a dimension of 27.5 cm (length)×6 cm (width)×0.7 cm (thickness).

The carrier was laid on the conveyor belt; at first, the liquid mixture of the cells and glutaraldehyde was sprayed by the spraying component of the first spraying-kneading component on the surface of the carrier; the carrier was kneaded by the kneading component (including one or more kneading rolls) of the first spraying-kneading component to distribute the liquid mixture evenly on the surface of the carrier; then, 0.25% (w/v) PEI solution was sprayed on the surface of the carrier by the spraying component of the second spraying-kneading component; the carrier was kneaded by the kneading component (including one or more kneading rolls, preferably, the kneading rolls that have grooves) of the second spraying-kneading component; at last, the excess liquid was removed by the squeezing component (including one or more squeezing rolls). In this way, the conveyor belt completed one time of carrier transportation. After repeating the above immobilization steps seven times, the immobilized E. coli cell was dried under room temperature overnight. The weight of dried immobilized E. coli cell containing expressed glucose isomerase was 6.06 g.

Ten mg of immobilized E. coli. cell containing expressed glucose isomerase was added with 1 ml of 45% glucose solution (containing 4 mM magnesium sulphate, 180 ppm sodium pyrosulfite, pH 7.5, pre-heated at 60° C.). The reaction mixture was shaked at 60° C. at 1400 rpm for 10 minutes and was terminated by immersing the reaction mixture in ice bath for 5 minutes. The reaction mixture was diluted ten times by deionized water and the amount of fructose was determined according to Table 1. One mg/ml of fructose (Sigma-Aldrich Company Ltd) standard solution was prepared by deionized water; 2.4% (w/v) of cysteine hydrochloride (Guangzhou Everwin Bio-tech. Co. Ltd.) solution was prepared by deionized water; 1.2 mg/ml of carbazole (Sigma-Aldrich Company Ltd) alcoholic solution was prepared by 100% ethanol.

TABLE 1

| Components/μl | Blank | Standard | | | | Substrate control | Samples |
|---|---|---|---|---|---|---|---|
| Deionized water | 50 | 40 | 30 | 20 | 10 | 25 | 25 |
| Frustose standard solution | 0 | 10 | 20 | 30 | 40 | 0 | 0 |
| Diluted reaction mixture | 0 | 0 | 0 | 0 | 0 | 25 | 25 |
| Cysteine hydrochloride solution | 30 | | 30 | | | 30 | 30 |
| Carbazole alcoholic solution | 30 | | 30 | | | 30 | 30 |
| 70% Sulphuric acid | 1000 | | 1000 | | | 1000 | 1000 |

The absorbance at 560 nm was measured

One unit was defined as 1 μmol of fructose produced per minutes according to the Table 1. The specific activity of the immobilized E. coli cell containing expressed glucose isomerase in Example 1 was determined as 385 U/g.

Example 2

Immobilization of Glucose Isomerase

Twenty five g of E. coli cells containing expressed glucose isomerase was resuspended in 100 ml deionized water. The cell was disrupted after complete resuspension, using a high pressure homogenizer and was centrifuged for 30 minutes at 13000 rpm to obtain the supernatant. The protein concentration of the supernatant was diluted to 10 mg/ml by deionized water, added 20 ml of 1% glutaraldehyde solution and stirred for 10 minutes. The device that has two spraying-kneading components described above was used to prepare the immobilized enzymes. The procedure included the following steps:

The liquid mixture of glucose isomerase and glutaraldehyde was sprayed by the spraying component of the first spraying-kneading component at the flow rate of 60 ml/min; 0.25% (w/v) PEI solution was sprayed by the spraying component of the second spraying-kneading component at the flow rate of 45 ml/min; the speed of conveyor belt was set to 80 cm/min. The carrier was 1 g of melamine foam with dimension 25.2 cm (length)×6 cm (width)×0.7 cm (thickness).

The carrier was laid on the conveyor belt; at first, the liquid mixture of glucose isomerase and glutaraldehyde was sprayed by the spraying component of the first spraying-kneading component on the surface of the carrier; the carrier was kneaded by the kneading component (including one or more kneading rolls) of the first spraying-kneading component to distribute the liquid mixture evenly on the surface of the carrier; then, 0.25% (w/v) PEI solution was sprayed on the surface of the carrier by the spraying component of the second spraying-kneading component; the carrier was kneaded by the kneading component (including one or more kneading rolls, preferably, the kneading roll that have groove) of the second spraying-kneading component; at last, the excess liquid was removed by the squeezing component (including one or more squeezing rolls). In this way, the conveyor belt completed one time of carrier transportation. After repeating the above immobilization steps thirteen times, the immobilized glucose isomerase was dried under room temperature overnight. The weight of dried immobilized glucose isomerase was 3.74 g.

The immobilized glucose isomerase of 8.6 mg was taken for the measurement of the specific activity. The specific activity of immobilized glucose isomerase was determined as 451 U/g by the method in Example 1.

It should be noted that the immobilization method in the embodiment uses a crosslinker to crosslink the proteins, enzymes or cells first, followed by using a flocculant to precipitate the proteins, enzymes or cells on the carrier. Using this procedure, only two spraying-kneading components are sufficient to spray the liquid mixture of the proteins, enzymes or cells and the crosslinker followed by the flocculant and hence the device and the immobilization operation are simplified. In practical application, another immobilization method can be used. For example, firstly, proteins, enzymes or cells are distributed evenly on the surface of the carrier; secondly, a flocculant is added to precipitate the proteins, enzymes or cells on the carrier; thirdly, a crosslinker is added to crosslink and immobilize the proteins, enzymes or cells. In the case that this immobilization method is employed, three spraying-kneading components are necessary to spray the proteins, enzymes or cells followed by the flocculant and the crosslinker.

To sum up, the immobilization method provided in the invention uses the device provided in the invention to prepare the immobilized proteins, enzymes or cells to achieve the industrial batch production of the immobilized proteins, enzymes or cells.

The specific embodiments presented above are used for illustration of the principle of the invention only and are not intended to restrict the invention. A person skilled in the art understands that various modifications and changes can be made to the present invention without departing from the concept and spirit of the invention, and the modifications and changes also fall within the scope of the present invention.

The invention claimed is:

1. A device for preparation of immobilized enzymes on a carrier, comprising:
   i) a conveyor belt that transports a carrier for immobilizing enzymes;
   ii) two or more spraying-kneading components that are arranged in sequence along a transport path of the conveyor belt; each of the spraying-kneading components including the following components in sequence: (1) a spraying component that sprays a pre-prepared liquid for the immobilization of the enzymes on a surface of the carrier; (2) a kneading component that distributes the pre-prepared liquid evenly on the surface of the carrier;
   iii) a squeezing component that removes excess liquid remaining on the surface of the carrier after the carrier passes through the spraying-kneading components,
   wherein each of the kneading components comprises a plurality of kneading rollers arranged above the conveyor belt,
   wherein one or more of the plurality of kneading rollers comprises a smooth surface and one or more of the plurality of kneading rollers comprises uniformly distributed grooves in a surface thereof, and the kneading rollers having smooth surfaces are arranged upstream of the kneading rollers having grooves,
   wherein the kneading rollers are arranged along the transport path of the conveyor belt continuously and in sequence,
   wherein the kneading rollers roll over the surface of the carrier when the carrier passes through a gap between the kneading roller and the conveyor belt;
   wherein the grooves are strip-shaped, a lengthwise direction of the grooves is parallel to an axial direction of the kneading rollers, and the grooves are distributed evenly in a circumferential direction of the kneading rollers, or the grooves are ring-shaped, a circumferential direction of the grooves is perpendicular to the axial direction of the kneading rollers, and the grooves are distributed evenly in the axial direction of the kneading rollers, and
   wherein for two adjacent kneading rollers that have the ring-shaped grooves, the ring-shaped grooves of one of the adjacent kneading rollers are offset by a width of one groove with respect to the ring-shaped grooves of the other kneading roller respectively.

2. The device according to claim 1, wherein the spraying component of each of the spraying-kneading components includes one or more sprayers that are provided above the conveyor belt, the one or more sprayers arranged continuously and in sequence along the transport path of the conveyor belt, and wherein the sprayers in the same spraying-kneading component spray the pre-prepared liquid of the same type.

3. The device according to claim 2, wherein the sprayers comprise a sparger pipe, a spray nozzle or an overflow groove.

4. The device according to claim 3, wherein the spray nozzle comprises an atomizer nozzle or a flow nozzle.

5. The device according to claim 3, wherein the sparger pipe comprises holes for spraying the pre-prepared liquid and a wire gauze is covered on the holes.

6. The device according to claim 2, wherein the spraying component comprises one or more first height adjustment mechanism sets that adjust heights of the sprayers above the conveyor belt, and wherein each of the first height adjustment mechanism sets includes two first height adjustment mechanisms that are provided on both ends of the sprayer that corresponds to the first height adjustment mechanism set.

7. The device according to claim 1, wherein the shape of the grooves is trapezoidal, rectangular or tapered.

8. The device according to claim 1, wherein the kneading component comprises one or more second height adjustment mechanism sets that adjust heights of the kneading rollers above the conveyor belt, and each of the second height adjustment mechanism sets includes two second height adjustment mechanisms that are provided on both ends of the kneading roller that corresponds to the second height adjustment mechanism set.

9. The device according to claim 1, wherein the squeezing component comprises one or more squeezing rollers that are provided above the conveyor belt, the one or more squeezing rollers arranged along the transport path of the conveyor belt continuously and in sequence, and wherein each of the squeezing rollers rolls over the surface of the carrier to remove the excess liquid when the carrier passes through a gap between the squeezing roller and the conveyor belt.

10. The device according to claim 1, wherein the squeezing component comprises one or more squeezing roller sets that are provided continuously and in sequence at a terminal end of the conveyor belt, the one or more squeezing roller sets arranged along the transport path of the conveyor belt; each of the squeezing roller sets includes an upper squeezing roller and a lower squeezing roller, wherein the carrier that reaches a terminal end of the conveyor belt passes through a gap between the upper squeezing roller and the lower squeezing roller by the rotation of the lower squeezing roller, a linear velocity of the lower squeezing roller is equal to that of the conveyor belt, and the upper squeezing roller rolls over the carrier to remove the excess liquid when the carrier passes therefrom.

11. The device according to claim 9, wherein the squeezing component comprises one or more third height adjustment mechanism sets that adjust heights of the squeezing rollers above the conveyor belt, and each of the third height adjustment mechanism sets includes two third height adjustment mechanisms that are provided on both ends of the squeezing roller that corresponds to the third height adjustment mechanism set.

12. The device according to claim 10, wherein the squeezing component comprises one or more third height adjustment mechanism sets that adjust heights of the upper squeezing rollers above the lower squeezing rollers, and each of the third height adjustment mechanism sets includes two third height adjustment mechanisms that are provided on both ends of the squeezing roller that corresponds to the third height adjustment mechanism set.

13. The device according to claim 10, wherein the device further comprises a motor that provides power and a transmission mechanism that delivers the power from the motor to the lower squeezing roller and the conveyor belt.

14. The device according to claim 9, wherein the device further comprises a motor that provides power and a transmission mechanism that delivers the power from the motor to the conveyor belt.

15. The device according to claim 1, wherein the device further comprises a recovery support plate that supports the carrier after the carrier passes through the squeezing component.

16. The device according to claim 1, wherein the carrier is made of a porous organic foam material containing open pores.

17. The device according to claim 16, wherein the carrier is made of melamine.

18. The device according to claim 1, wherein the carrier is sheet-shaped with a thickness of 0.1-2 cm.

19. A method for preparation of immobilized enzymes on a carrier, comprising using the device according to claim 1, to prepare immobilized enzymes on a carrier.

20. The method according to claim 19, wherein the method comprises the following steps:

S1. preparing a liquid mixture of enzymes and a crosslinker by crosslinking the enzymes using the crosslinker;

S2. spraying the liquid mixture on the surface of the carrier and distributing the liquid mixture evenly on the surface of the carrier;

S3. spraying a flocculant on the surface of the carrier and distributing the flocculant evenly on the surface of the carrier;

S4. removing the excess liquid remaining on the surface of the carrier.

21. The method according to claim 20, wherein the concentration of the enzymes is 0.3%-30%.

22. The method according to claim 20, wherein the crosslinker is a polyaldehyde compound.

23. The method according to claim 22, wherein the polyaldehyde compound is glutaraldehyde or dialdehyde starch.

24. The method according to claim 20, wherein the flocculant is polyethyleneimine (PEI) or chitosan.

* * * * *